United States Patent [19]
Zadeh

[11] Patent Number: 5,769,873
[45] Date of Patent: Jun. 23, 1998

[54] METER FOR MEASURING BATTERY CHARGE DELIVERED IN AN IMPLANTABLE DEVICE

[75] Inventor: Ali Enayat Zadeh, Sierra Madre, Calif.

[73] Assignee: Pacesetter, Inc., Sylmar, Calif.

[21] Appl. No.: 730,262

[22] Filed: Oct. 15, 1996

[51] Int. Cl.[6] .................................................... A61N 1/378
[52] U.S. Cl. ............................................................. 607/29
[58] Field of Search ............................... 607/29; 320/44, 320/48

[56] References Cited

U.S. PATENT DOCUMENTS

| | | | |
|---|---|---|---|
| 4,290,429 | 9/1981 | Blaser | 607/29 |
| 5,092,330 | 3/1992 | Duggan | 607/29 |
| 5,193,538 | 3/1993 | Ekwall. | |
| 5,325,041 | 6/1994 | Briggs | 320/44 |
| 5,336,242 | 8/1994 | Zadeh | 607/11 |
| 5,458,624 | 10/1995 | Renirie et al. | 607/29 |
| 5,496,353 | 3/1996 | Grandjean et al. | 607/29 |

*Primary Examiner*—Scott M. Getzow

[57] ABSTRACT

An improved apparatus and method are described for providing a measurement of the charge depleted from a battery used in an implantable device such as a cardiac pacemaker. The measurement is provided not by measuring the voltage level or impedance of the battery, but rather by continuously measuring the electrical current drawn from the battery and integrating that measured current over an integration time period. A precision current-sensing resistor provides a sense signal having a voltage that varies according to the magnitude of current being drawn, and this sense signal is integrated using a voltage-controlled oscillator circuit and counter, which are implemented using CMOS circuitry arranged in a switched-capacitor topology.

18 Claims, 4 Drawing Sheets

METER FOR MEASURING BATTERY CHARGE DELIVERED IN AN IMPLANTABLE DEVICE

FIELD OF THE INVENTION

The present invention relates generally to implantable devices and, more particularly, to a battery charge delivery meter for use in such an implantable device.

BACKGROUND OF THE INVENTION

Miniature batteries are widely used for powering biomedical devices that are implantable in a living body. For example, cardiac pacemakers that monitor a patient's heart, and provide stimulating pulses to the heart, are powered by such miniature batteries. Because such implantable batteries operate in life-preserving applications, it is extremely important always to know their remaining charge. This enables the physician to prescribe procedures to replace the battery and/or the pacemaker at an appropriate time.

Accordingly, battery charge meters have been used to provide measurements of the remaining charge of implanted batteries. Many implantable cardiac pacemakers are equipped with telemetry devices that transmit important information about the device, including information relating to the battery's remaining charge. Such information is transmitted to an external programmer device.

Conventional techniques for measuring the remaining charge of miniature batteries typically rely on the relationship between the battery's supply voltage and supply current. As is well known, this relationship is primarily dictated by the battery's chemistry. For example, Ni—Cad batteries, widely used in portable electronic devices, have a specific discharge characteristic in which the battery's voltage remains substantially constant for nearly the entire range of charge, but then rapidly rolls off to a low supply voltage when the charge is nearly depleted. Other types of batteries, such as lithium-iodine, alkaline, zinc-air, or metal-hydride batteries, also have characteristic relationships between their supply voltages and supply currents that are specific to their particular chemistries.

Battery charge metering techniques that rely on the battery's chemistry-related characteristics do not always provide accurate information about the battery's remaining charge. Factors such as processing variations during battery assembly, lamination, and packaging can prevent the battery's chemistry-related characteristics from providing the resolution needed for accurately measuring remaining battery charge.

Another conventional technique used for indicating the remaining charge of an implantable battery monitors the battery's impedance. It provides a binary indication as to whether or not the battery's recommended replacement time has been reached. However, until that recommended replacement time has been reached, this technique provides minimal information about the battery's remaining charge. Furthermore, battery impedance can vary according to ambient environmental factors, which can result in erroneous estimations of remaining battery charge.

To prescribe timely battery removal and replacement procedures, the physician requires an extremely accurate measurement of the battery's remaining charge. Accordingly, there is a need for a battery charge meter that can accurately indicate the amount of depleted battery charge. Furthermore, there is a need for such battery charge meter to include circuitry that is readily integratable with existing circuitry of the implantable device. The present invention satisfies these and other needs.

SUMMARY OF THE INVENTION

The present invention resides in a battery charge delivery meter, and a related method, that monitors the electrical current being supplied by a battery to a load circuit and provides an accurate measurement of the depleted charge. The meter itself consumes minimal charge from the battery, and it is readily integratable with the load circuit, making it suitable for use in an implantable biomedical device such as a cardiac pacemaker. The battery charge delivery meter includes a sensor that is coupled to the battery, for providing a sense signal indicative of the electrical current being drawn from the battery. The sense signal is supplied to an integrator, to produce a measurement of the depleted battery charge over an integration time period.

In a more detailed feature of the invention, the integrator includes a voltage-controlled oscillator (VCO) circuit that generates a VCO signal, preferably in the form of a pulse sequence, where each pulse has a duration corresponding to a discrete quantity of depleted charge. The integrator also includes a counter that counts the pulses, to produce the measurement of the depleted charge. The VCO circuit can advantageously be implemented using CMOS switched-capacitor circuits, which minimizes battery charge consumption. The VCO circuit can include an integrator amplifier that integrates the sense signal, to produce a ramp signal, and a comparator amplifier that compares the ramp signal with a prescribed threshold. When the ramp signal is determined to have reached the threshold, the comparator conditions the integrator amplifier to reinitiate its integration, and the VCO signal changes its state each time the threshold is reached.

Other features and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENT

Figure 1:
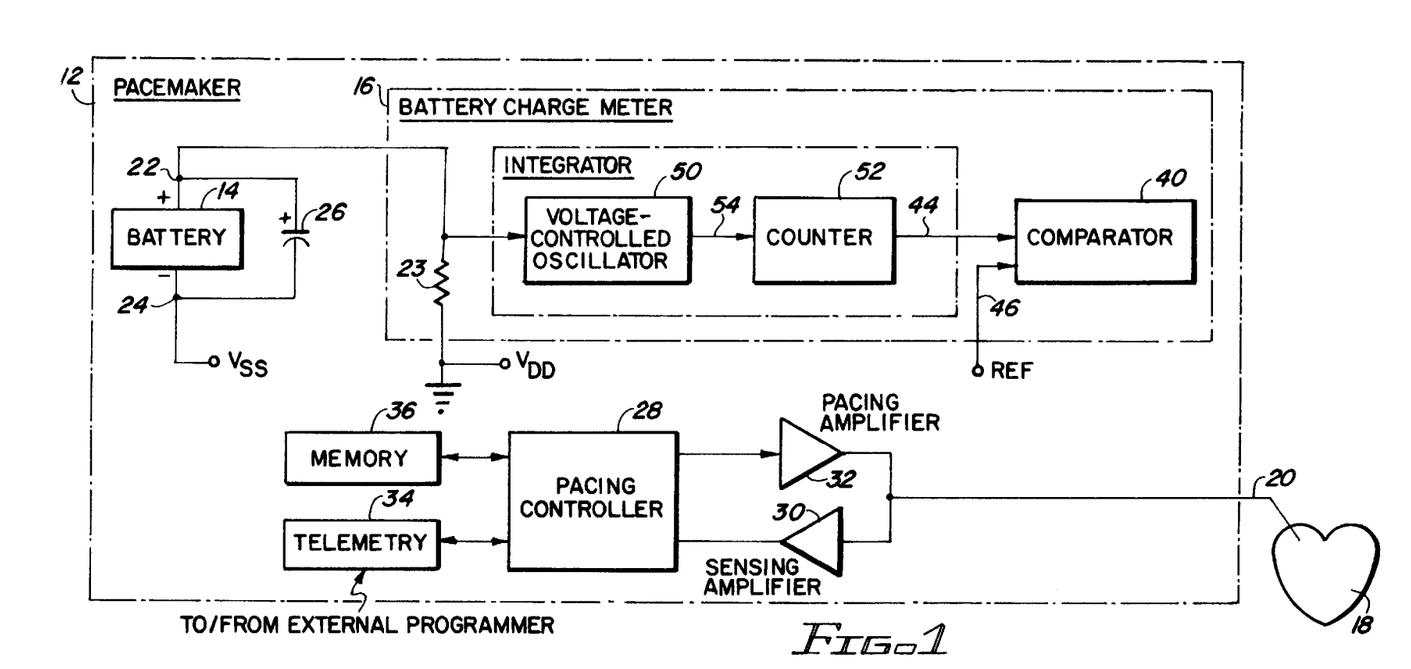
FIG. 1 is a simplified block diagram of a cardiac pacemaker that incorporates a battery charge delivery meter according to the present invention.

With reference now to the drawings, and particularly to FIG. 1, there is shown an implantable biomedical device in the form of a cardiac pacemaker 12 that carries a miniature battery 14 whose discharge is monitored by a battery charge meter 16. The pacemaker couples to a patient's heart 18 via an electrogram lead 20, which carries electrical signals indicative of cardiac activity from the heart to the pacemaker and further carries electrical pacing pulses from the pacemaker to the heart.

The battery 14 advantageously can take the form of a lithium-iodine battery, which is widely used in implantable devices of this kind. One such battery is sold by Great Wilson Batch Incorporated having suitable physical dimensions and characteristics for being safely implanted into the human body. The battery has a predetermined initial charge capacity, typically on the order of one ampere-hour (A-h). The battery's positive terminal 22 couples through a small, precision current-sensing resistor 23 to ground potential, which is designated VDD, and its negative terminal 24 provides power to the pacemaker circuitry, designated VSS. A large capacitive load 26 couples across the battery, to dampen the effect of any sudden variations in the current being drawn by the pacemaker circuitry and thereby to maintain a more stable voltage level.

The pacemaker 12 incorporates circuitry fabricated using well known complementary metal-oxide semiconductor (CMOS) technology. This circuitry includes a pacing controller 28, which receives monitoring signals from the patient's heart 18 via the lead 20 and a sense amplifier 30, and which transmits pacing pulse signals to the heart via a pacing amplifier 32 and the lead 20. As is conventional, a telemetry circuit 34 communicates with an external programmer (not shown), selectively transmitting either real-time signals received from the heart or accumulated data retrieved from a memory 36. The telemetry circuit also receives reprogramming information from the external programmer, for storage in the memory. The pacing controller executes a software, or firmware, code stored in the memory, to provide a specified therapy to the heart. The memory also stores parameters including battery charge parameters, such as an initial measurement of battery charge, which may be indicative of the battery capacity.

Because the pacemaker circuitry generally draws current from the battery 14 on a continuous basis, the battery's limited stored charge will be continuously depleted. Unless corrective action is taken, the battery eventually would be incapable of providing the electrical current required for the circuitry to function properly. It is, therefore, important for the physician to have information about the amount of charge remaining in the battery, so that appropriate surgical procedures can be carried out to remove and replace the battery and/or the entire pacemaker 12.

The pacemaker's battery charge meter 16 is configured to measure the current drawn from the battery 14, on a continuous basis, and to provide a signal indicating the remaining battery charge. More particularly, the battery charge meter 16 includes the precision resistor 23, an integrator 38, and a comparator 40. The resistor is connected between the battery's positive terminal 22 and the ground potential, $V_{DD}$.

The node between the resistor 23 and the battery's positive terminal 22 thus carries a positive voltage that is a measurement of the instantaneous electrical current being drawn from the battery 14. This voltage is supplied as a sense signal on line 42 to the integrator 38, which provides a digital charge depletion signal that varies according to the amount of charge depleted from the battery. The charge depletion signal is supplied on line 44 to the comparator 40, for comparison with a digital reference signal representing the battery's initial charge capacity. That digital reference signal is supplied to the comparator on line 46, from a battery charge circuit (not shown). Based on the comparison, the comparator outputs a battery charge signal on line 48, which represents the amount of charge remaining in the battery.

It will be appreciated that the comparison function performed by the comparator 40 alternatively could be performed by a suitable microcontroller, executing a suitable programming code. Under this alternative configuration, the battery's initial charge capacity may be programmably or permanently embedded in the memory 36.

The integrator 38, which integrates the sense signal produced by the precision resistor 23, is shown to include a voltage-controlled oscillator (VCO) circuit 50 and a digital counter 52. In practice, the capacitive load 26 causes the sense signal to have very limited fluctuations and to be characterized as a near dc potential. The VCo circuit outputs a VCO signal having an instantaneous frequency corresponding to the level of the sense signal and, thus, to the instantaneous magnitude of the electrical current being drawn from the battery 14. Preferably, the VCO signal takes the form of a pulse sequence, in which the duration of each pulse represents a predetermined discrete quantity of depleted charge.

The VCO signal is supplied on line 54 to the digital counter 52, which accumulates a count representing the total amount of depleted battery charge. The counter can be fabricated using CMOS technology, and it can be configured to increment from a minimum reference (e.g., 0) or to decrement from a maximum reference (e.g., $2^n$, where n is the number of counter bits).

The VCO circuit 50 and digital counter 52 need to be sized to measure an electrical current as high as about 500 microamperes, and they preferably can accurately differentiate the current in steps as small as about 0.5 microamperes. Higher resolution is, of course, desirable if possible.

The following equations may be used to calculate the amount of depleted battery charge:

Calculation of the Battery Charge Delivered

The input voltage to the VCO circuit 50, $V_{in}(t)$, which is the sense signal on line 42, is determined by equation (1):

$$(1) V_{in}(t) = I(t)R_s,$$

where $R_s$=the resistance of the sense resistor, and where I(t)=Battery Current (time varying)

The frequency of the VCO signal on line 54 at time $t_i$, $F_{out}(t_i)$, is determined by equation (2):

$$(2) F_{out}(t_i) = K_{VCO}V_{in}(t_i) = K_{VCO}R_sI(t_i),$$

where $K_{VCO}$ is the VCO conversion constant $$\left[ \frac{HZ}{V} \right].$$

The output of the counter 52, i.e., the count of depleted charge, is given by equation (3):

$$\text{Count} = \sum_{t_i=0}^{t_i=T} F_{out}(t_i)\Delta t_i = \sum_{t_i=0}^{t_i=T} K_{VCO}R_sI(t_i)\Delta t_i = K_{VCO}R_sQ_{delivered}, \quad (3)$$

$$Q_{delivered} = \frac{\text{Count}}{K_{VCO} \cdot R_s}, \quad (4)$$

$$\text{where } Q_{delivered} = \sum_{t_i=0}^{t_i=T} I(t_i)\Delta t_i$$

Therefore, from the value of the accumulated count and from the values $K_{VCO}$ and $R_s$, the amount of charge that has been depleted from the battery 14 can be estimated.

As an exemplary arrangement, it is assumed that the sense resistor is:

$$R_s = 500\Omega = 500\left(\frac{V}{A}\right)$$

and the VCO circuit conversion constant is:

$$K_{VCO} = 100\left(\frac{HZ}{V}\right)$$

Thus, according to equation (4), the depleted charge is:

$$Q_{delivered} = \frac{\text{Count}}{R_s \cdot K_{VCO}} = \frac{\text{Count}}{50,000} \text{ (A - Sec)}$$

Assuming a predetermined battery charge of 1 A-h, then:

$$Q_{Battery} = 1A\text{-}h = 3600(A\text{-}Sec)$$

Thus, the maximum accumulated count of the counter 52, at the end of the life of the battery 14, is given by equation 5:

$$(5) \text{Count}(max) = 50,000 \times 3600 \approx 2^{28}$$

Thus, a 28-bit counter is needed to cover the entire range of the battery's useful life. To reduce the number of counter bits, the pacing controller 28 can be programmed to store periodic counts of a lesser number of counter bits (e.g., 8 counter bits) and to store the counter values in the memory 36. When signaled to measure battery charge, the controller can add the periodically stored counts, to determine remaining battery charge.

For ease of circuit integration, the physical implementation of the VCO circuit 50 and the counter 52 preferably utilize the same CMOS integrated circuit technology as that used in fabricating the remainder of the pacemaker circuitry. The use of CMOS circuitry also allows the battery charge meter 16 to operate under low supply voltage conditions, even as low as 1.8 volts. The battery charge meter preferably consumes minimal battery charge, e.g., less than 100 nanoamperes. To help achieve this, the VCO circuit is implemented using switched-capacitor techniques.

Figure 2:
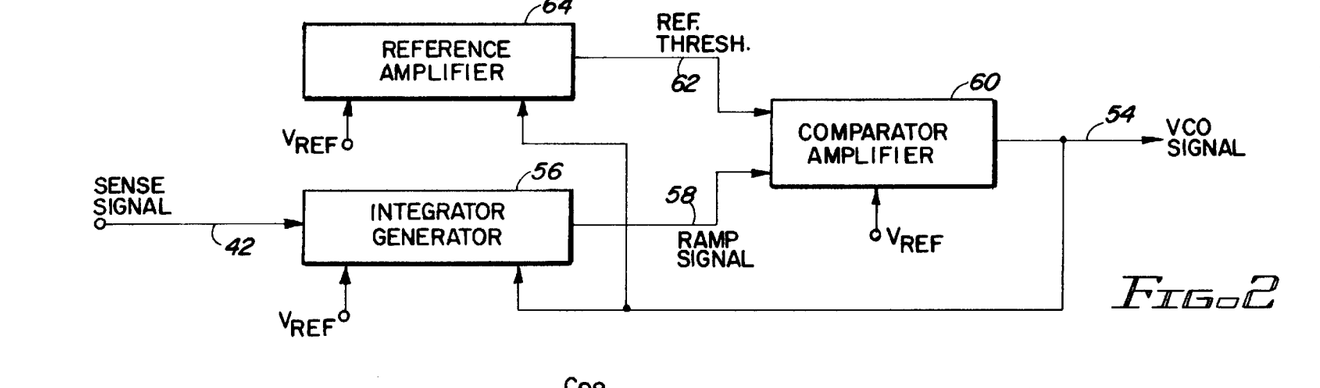
FIG. 2 is a block diagram of the voltage-controlled oscillator (VCO) circuit that is part of the cardiac pacemaker of FIG. 1.

A simplified block diagram of the VCO circuit 50 is shown in FIG. 2. The VCO circuit produces the VCO signal on line 54, which takes the form of a pulse sequence in which the duration of each pulse corresponds to a fixed amount of charge being depleted from the battery 14.

The VCO circuit 50 includes an integrator amplifier 56 that integrates the sense signal $V_{in}$ supplied on line 42, to produce a ramp signal $V_{ramp}$ whose magnitude increases monotonically at a rate corresponding to the magnitude of the sense signal, i.e., the instantaneous magnitude of the electrical current being drawn from the battery 14. This ramp signal is supplied on line 58 to a comparator amplifier 60, where it is compared with a prescribed reference threshold supplied on line 62 from a reference generator 64. The digital VCO signal, which is output by the comparator amplifier on line 54, changes state when the ramp signal reaches the threshold.

The VCO signal is coupled via line 54 back to the integrator amplifier 56, such that a change in state inverts the amplifier's polarity and causes the ramp signal $V_{ramp}$ to ramp in the opposite direction. The VCO signal also is coupled back to the reference generator 64, such that a change in state inverts the polarity of the prescribed reference threshold $V_{thresh}$. The comparator amplifier 60 then compares the oppositely sloped ramp signal with the inverted threshold. When the threshold finally is reached, the comparator amplifier again reverses the state of the VCO signal, and feedback of the VCO signal to the integrator amplifier and reference amplifier causes their polarities again to be inverted.

Figure 3A:
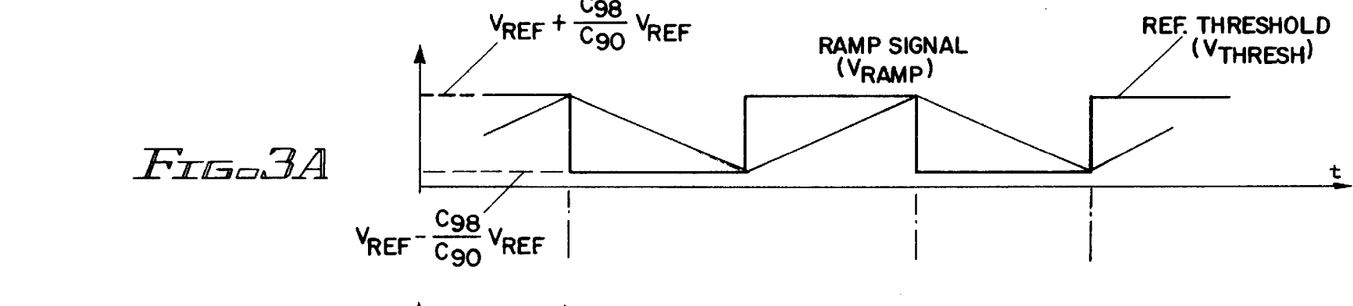
FIGS. 3A and 3B are timing diagrams of certain signals present in the VCO circuit of FIG. 2.
Figure 3B:
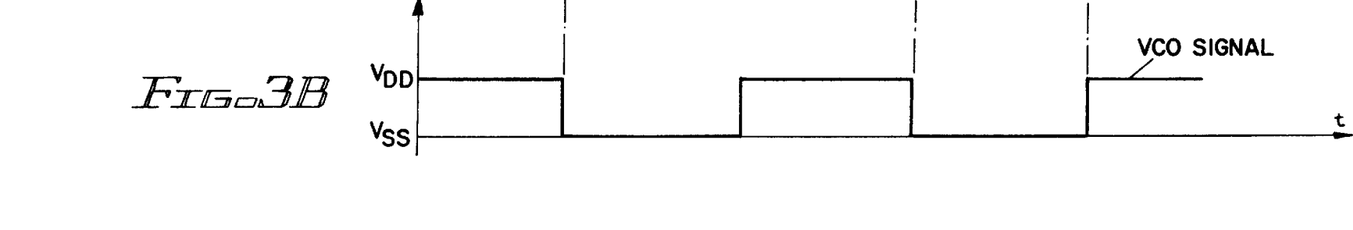

This process continues, with the ramp signal $V_{ramp}$ on line 58 alternately sloping upwardly and downwardly, and with the reference threshold $V_{thresh}$ on line 62 alternately being high and low. The VCO signal on line 54 changes its state each time the ramp signal reaches the threshold. The ramp signal and the reference threshold are depicted in FIG. 3A, and the VCO signal is depicted in FIG. 3B.

It will be appreciated that, if the sense signal $V_{in}$ on line 42 indicates that a relatively high electrical current is being drawn from the battery 14, then the slope of the ramp signal $V_{ramp}$ on line 58 will be relatively steep and the VCO signal on line 54 will have a relatively high frequency. On the other hand, if the sense signal indicates that a relatively low electrical current is being drawn from the battery, then the slope of the ramp signal will be relatively shallow and the VCO signal will have a relatively low frequency.

Figure 4:
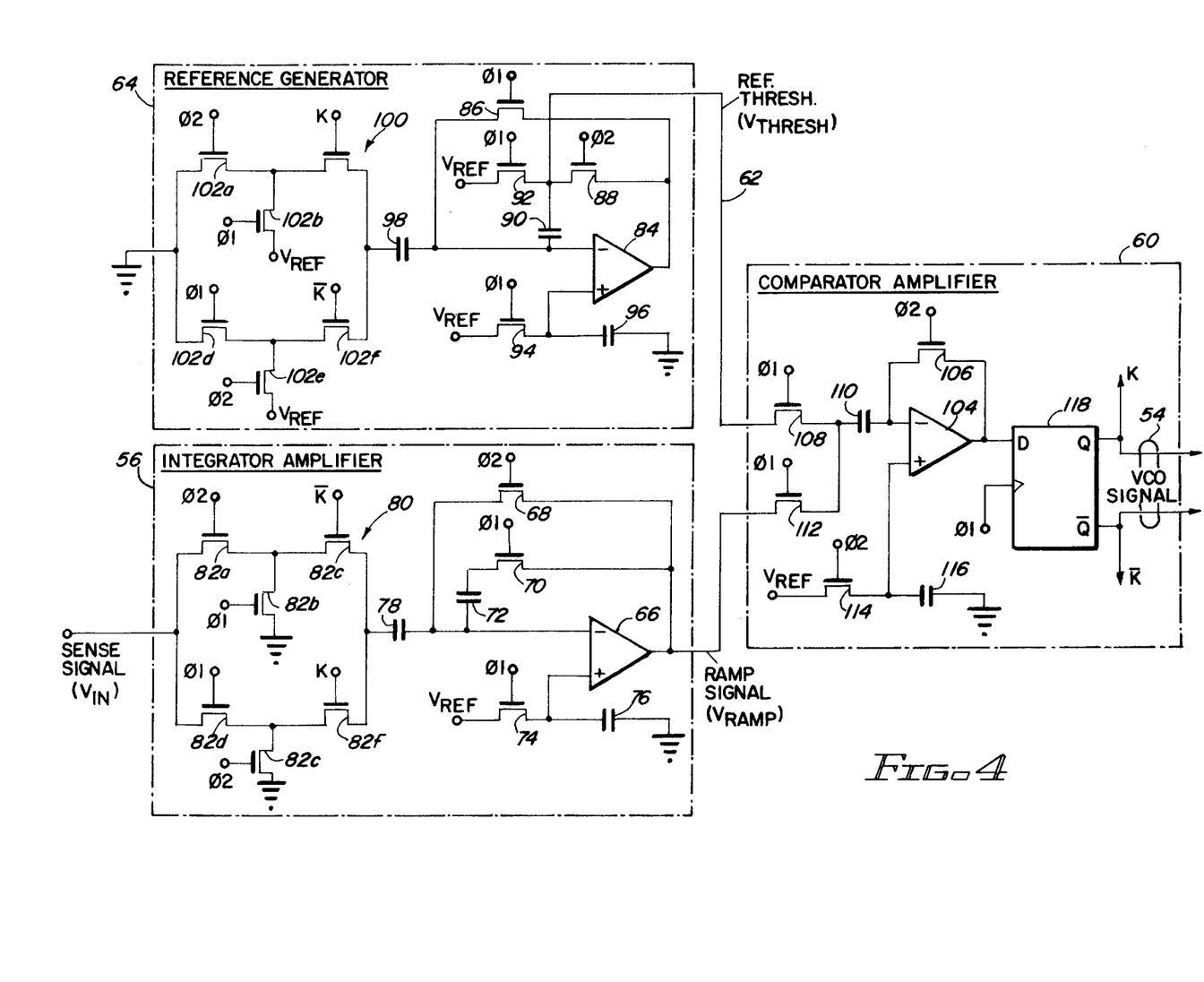
FIG. 4 is a schematic circuit diagram of a first embodiment of the VCO circuit of FIG. 2, implemented using switched-capacitor CMOS circuitry.

FIG. 4 is a more detailed, schematic diagram of the VCO circuit 50, showing its implementation using CMOS circuitry. Use of this circuitry makes the circuit compatible with the remaining circuitry of the pacemaker 12. The circuit uses a switched-capacitor topology, including operational amplifiers (op amps), field-effect transistors (FETs), and capacitors. As is known, such circuitry consumes minimal electrical power and requires minimal circuit real estate.

Figure 5:
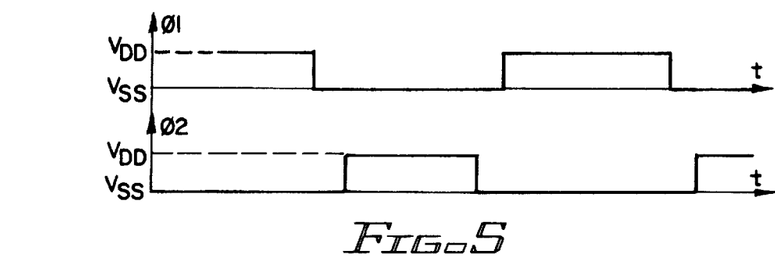
FIG. 5 is a timing diagram of clock signals used in the VCO circuit of FIG. 4.

The VCO circuit 50 is configured to control its switched-capacitor circuitry using a pair of oppositely phased, non-overlapping clock signals $\phi1$ and $\phi2$ (see FIG. 5). Use of such clock signals is conventional in circuitry of this kind, and it enables the adverse effects of voltage offsets that inherently arise in CMOS op amps to be eliminated. Using this approach, the CMOS circuitry operates alternately in two different modes, i.e., an auto-zeroing mode and a conversion mode. During the auto-zeroing mode, certain voltage levels are established that reflect the magnitude of such offsets, whereas during the succeeding conversion mode, signals are processed in a way that automatically cancels the effects of the offsets. A brief dead time separates the two clock signals $\phi1$ and $\phi2$, to prevent any possibility of an overlap.

The integrator amplifier 56, the reference generator 64, and the comparator amplifier 60 all incorporate op amps and thus are advantageously controlled using the non-overlapping clock signals $\phi1$ and $\phi2$. These clock signals control the operating mode of the circuits, i.e., auto-zeroing mode or conversion mode. Also controlling the reference amplifier and the integrator amplifier are complementary digital control signals K and $\overline{K}$, which correspond to the VCO signal output on line 54. These control signals control the circuits' polarity, for the reasons described briefly above. Also supplied to all three circuits is a predetermined voltage reference $V_{ref}$.

The structure and operation of the integrator amplifier 56 of the VCO circuit 50 will be described first. The integrator amplifier includes an op amp 66 configured with its output terminal connected to its inverting input terminal via both a FET 68 and a series-connected FET 70 and capacitor 72. The op amp's non-inverting input terminal is connected to the voltage reference $V_{ref}$ via a FET 74 and to ground via a capacitor 76. The op amp's inverting input terminal also is connected via a capacitor 78 to an input stage 80. This input stage includes an array of FETs 82a–82f, which, under the control of the control signals K and $\overline{K}$ and the clock signals $\phi 1$ and $\phi 2$, selectively provides a voltage input that corresponds either to the sense signal $V_{in}$ on line 42 or to ground.

If the control signal $\overline{K}$ is assumed initially to be high (in which case the control signal K is low), then the ramp signal $V_{ramp}$ to be output by the integrator amplifier 56 on line 58 is made to have a positive slope. Further, if the clock signal $\phi 2$ is assumed initially to be high (in which case the clock signal $\phi 1$ is low), then the integrator amplifier operates in the auto-zeroing mode. In that mode, the op amp's output terminal is connected to the op amp's inverting input terminal through the FET 68. In addition, the sense signal $V_i$ on line 42 is coupled through the FETs 82a and 82c to the capacitor 78, and the voltage reference $V_{ref}$ is coupled through the FET 74 to the capacitor 76 and to the non-inverting input terminal of the op amp 66.

At this time, the op amp 66 operates in its linear mode, with the voltage at its output terminal corresponding to the voltage reference $V_{ref}$ plus an unknown offset voltage $V_{off}$, which is an inherent feature of the op amp. A voltage drop of $(V_{ref}+V_{off}-V_{in})$ thereby is established across the capacitor 78.

Thereafter, when the clock signal $\phi 2$ transitions to its low state (and the clock signal $\phi 1$ transitions to its high state), the integrator amplifier 56 will advance to its conversion mode of operation. At this time, a ground reference will be coupled through the FETs 82b and 82c to the capacitor 78, and the op amp's output terminal will be coupled through the FET 70 to the capacitor 72. The voltage reference $V_{ref}$ will remain applied to the op amp's non-inverting input terminal, from the capacitor 76.

At this time, the op amp 66 will endeavor to remain operating in its linear mode, with the voltage level at the op amp's inverting input terminal remaining at its prior value of $V_{ref}+V_{off}$. To achieve this condition, electrical charge must be transferred from the capacitor 78 to the capacitor 72. The amount of charge transferred is equal to the capacitance of the capacitor 78 multiplied by the voltage level of the sense signal $V_{in}$. The voltage level at the far terminal of the capacitor 72, which corresponds to the ramp signal $V_{ramp}$ present at the op amp's output terminal, then is given by the following equation (6):

$$V_{ramp}(n)=V_{ramp}(n-1)+(C_{78}/C_{72})V_{in}(n) \qquad (6)$$

where $V_{ramp}(n-1)$ and $V_{ramp}(n)$ are the voltage levels of the ramp signal on line 58 at times (n-1) and n, respectively, where $C_{78}$ and $C_{72}$ are the capacitances of the capacitors 78 and 72, respectively, and where $V_{in}(n)$ is the voltage level of the sense signal on line 42 at time n.

Conversely, when the control signal $\overline{K}$ is low (and the control signal K therefore is high), the integrator amplifier 56 operates to provide a ramp signal $V_{ramp}$ on line 58 having a negative slope. In that case, the circuit again operates in its autozeroing mode when the clock signal $\phi 2$ is high and in its conversion mode when the clock signal $\phi 1$ is high.

In the auto-zeroing mode, the op amp's output terminal is connected to the op amp's inverting input terminal through the FET 68. In addition, a ground reference is coupled through the FETs 82e and 82f to the capacitor 78, while the voltage reference $V_{ref}$ is coupled through the FET 74 to the capacitor 76 and to the non-inverting input terminal of the op amp 66. At this time, the op amp operates in its linear mode, with the voltage at its output terminal corresponding to the voltage reference $V_{ref}$ plus the op amp's unknown offset voltage $V_{off}$. A voltage drop of $V_{ref}+V_{off}$ thereby is established across the capacitor 78.

Thereafter, when the clock signal $\phi 2$ transitions to its low state, and the clock signal $\phi 1$ transitions to its high state, the integrator amplifier 56 will advance to its conversion mode of operation. At this time, the sense signal $V_{in}$ will be coupled through the FETs 82d and 82f to the capacitor 78, and the op amp's output terminal will be coupled through the FET 70 to the capacitor 72. The voltage reference $V_{ref}$ will remain applied to the op amp's non-inverting input terminal, from the capacitor 76.

At this time, the op amp 66 will endeavor to remain operating in its linear mode, with the voltage level at the op amp's inverting input terminal remaining at its prior value of $V_{ref}+V_{off}$. To achieve this condition, electrical charge must be transferred from the capacitor 72 to the capacitor 78. The amount of charge transferred is equal to the capacitance of the capacitor 78 multiplied by the voltage level of the sense signal $V_{in}$. The voltage level at the far terminal of the capacitor 72, which corresponds to the ramp signal $V_{ramp}$ present at the op amp's output terminal, then is given by the following equation (7):

$$V_{ramp}(n)=V_{ramp}(n-1)-(C_{78}/C_{72})V_{in}(n). \qquad (7)$$

It thus will be appreciated that the gain of the integrator amplifier 56, positive or negative, is proportional to the ratio $C_{78}/C_{72}$.

The structure and operation of the reference generator 64 now will be described. The reference amplifier includes an op amp 84 configured with its output terminal connected to its inverting input terminal via both a FET 86 and a series-connected FET 88 and capacitor 90. The node between the FET 88 and capacitor 90 is connected via a FET 92 to the voltage reference $V_{ref}$, and this node provides the voltage reference threshold $V_{thresh}$ on line 62. The op amp's non-inverting input terminal is connected to the voltage reference $V_{ref}$ via a FET 94 and to ground via a capacitor 96.

The inverting input terminal of the op amp 84 also is connected via a capacitor 98 to an input stage 100. This input stage includes an array of FETs 102a–102f, which, under the control of the control signals K and $\overline{K}$ and the clock signals $\phi 1$ and $\phi 2$, selectively provides a dc voltage input of either $V_{ref}$ or ground.

If the control signal $\overline{K}$ is assumed initially to be high (in which case the control signal K is low), then the reference threshold $V_{thresh}$ to be output by the reference generator 64 on line 62 is made to be relatively high. Further, if the clock signal $\phi 1$ is assumed initially to be high (in which case the clock signal $\phi 2$ is low), then the reference amplifier operates in the auto-zeroing mode. In that mode, the op amp's output terminal is connected to the op amp's inverting input terminal through the FET 86. In addition, a ground potential is coupled through the FETs 102d and 102f to the capacitor 98, and the voltage reference $V_{ref}$ is coupled through the FET 94 to the capacitor 96 and to the non-inverting input terminal of the op amp 84. The reference voltage $V_{ref}$ also is coupled through the FET 92 to the reference amplifier's output line 62.

At this time, the op amp 84 operates in its linear mode, with the voltage at its output terminal corresponding to the voltage reference $V_{ref}$ plus an unknown offset voltage $V_{off}$, which is an inherent feature of the op amp. A voltage drop of $V_{ref}+V_{off}$ thereby is established across the capacitor 98, and a voltage drop of $V_{off}$ thereby is established across the capacitor 90.

Thereafter, when the clock signal φ1 transitions to its low state (and the clock signal φ2 transitions to its high state), the reference generator 64 will advance to its conversion mode of operation. At this time, the reference voltage $V_{ref}$ will be coupled through the FETs 102e and 102f to the capacitor 98, and the op amp's output terminal will be coupled through the FET 88 to the capacitor 90 and to the reference amplifier's output line 62. The voltage reference $V_{ref}$ will remain applied to the op amp's noninverting input terminal, from the capacitor 96.

At this time, the op amp 84 remains operating in its linear mode, with the voltage level at the op amp's inverting input terminal remaining at its prior value of $V_{ref}+V_{off}$. Electrical charge therefore is transferred from the capacitor 98 to the capacitor 90, until the op amp's output terminal reaches a voltage level given by the following equation (8):

$$V_{thresh}=V_{ref}+(C_{98}/C_{90})V_{ref}. \qquad (8)$$

where $C_{98}$ and $C_{90}$ are the capacitances of the capacitors 98 and 90, respectively, and where $V_{thresh}$ represents the reference threshold supplied on line 62 to the comparator amplifier 60.

Conversely, when the control signal $\overline{K}$ is low (and the control signal K therefore is high), the reference generator 64 operates to provide a relatively low reference threshold $V_{thresh}$ on line 62. In that case, the circuit again operates in its auto-zeroing mode when the clock signal φ1 is high and in its conversion mode when the clock signal φ2 is high.

In the auto-zeroing mode, the op amp's output terminal is connected to the op amp's inverting input terminal through the FET 86. In addition, the voltage reference $V_{ref}$ is coupled through the FETs 102b and 102c to the capacitor 98, while the voltage reference $V_{ref}$ also is coupled through the FET 94 to the capacitor 96 and to the non-inverting input terminal of the op amp 84. The reference voltage $V_{ref}$ also is coupled through the FET 92 to the reference amplifier's output line 62.

At this time, the op amp 84 operates in its linear mode, with the voltage at its output terminal corresponding to the voltage reference $V_{ref}$ plus the op amp's unknown offset voltage $V_{off}$. Voltage drops of $V_{off}$ thereby are established across the capacitor 98 and the capacitor 90.

Thereafter, when the clock signal φ1 transitions to its low state, and the clock signal φ2 transitions to its high state, the reference generator 64 will advance to its conversion mode of operation. At this time, the ground potential will be coupled through the FETs 102a and 102c to the capacitor 98, and the op amp's output terminal will be coupled through the FET 88 to the capacitor 90 and to the reference amplifier's output line 62. The voltage reference $V_{ref}$ will remain applied to the op amp's non-inverting input terminal, from the capacitor 96.

At this time, the op amp 84 remains operating in its linear mode, with the voltage level at the op amp's inverting input terminal remaining at its prior value of $V_{ref}+V_{off}$. Electrical charge therefore is transferred from the capacitor 98 to the capacitor 90, until the op amp's output terminal reaches a voltage level given by the following equation (9):

$$V_{out}=V_{ref}-(C_{98}/C_{90})V_{ref}. \qquad (9)$$

The structure and operation of the comparator amplifier 60 of the VCO circuit 50 now will be described. As discussed briefly above, the comparator amplifier compares the ramp signal $V_{ramp}$ on line 58 with the reference threshold $V_{thresh}$ on line 62, causing the VC0 signal on line 54 to undergo a state transition each time the ramp signal reaches the threshold.

As shown in FIG. 4, the comparator amplifier 60 includes an op amp 104 configured with its output terminal connected to its inverting input terminal via a FET 106. The reference threshold $V_{thresh}$ also is connected to the op amp's inverting input terminal, via a FET 108 and a capacitor 110, as is the ramp signal $V_{ramp}$, via a FET 112 and the capacitor 110. The op amp's non-inverting input terminal is connected to the voltage reference $V_{ref}$ via a FET 114 and to ground via a capacitor 116. Further, the op amp's output terminal is connected to the input terminal of a flip-flop 118, which is clocked by the clock signal φ1. The flip-flop's Q and $\overline{Q}$ output terminals provide the VCO signal on lines 54, which corresponds to the complementary control signals K and $\overline{K}$.

As with the reference generator 64 and the integrator amplifier 56, the comparator amplifier 60 operates alternately in an auto-zeroing mode and a conversion mode, under the control of the clock signals φ1 and φ2. In the auto-zeroing mode, which is the case when the clock signal φ2 is high (in which case the clock signal φ1 is low), the voltage reference $V_{ref}$ is applied to the op amp's non-inverting input terminal via the FET 106, and the op amp's output terminal is connected directly to the op amp's inverting input terminal.

At this time, the op amp 104 operates in a linear mode, with a voltage level of $V_{ref}$ plus an unknown offset voltage $V_{off}$ present at the op amp's inverting input terminal. Also at this time, the reference threshold $V_{thresh}$ on line 108 is applied to the capacitor 110, whereby a voltage drop equal to ($V_{ref}+V_{off}-V_{thresh}$) is produced across the capacitor 110.

Thereafter, when the clock signal φ2 goes low and the clock signal φ1 goes high, the comparator amplifier 60 operates in the conversion mode. At this time, the voltage reference $V_{ref}$ continues to be applied to the non-inverting input terminal of the op amp 104, from the capacitor 116, while the ramp signal $V_{ramp}$ on line 58 is now applied to the capacitor 110 via the FET 112.

If at this time the ramp signal $V_{ramp}$ is less than the reference threshold $V_{thresh}$ then the voltage level applied by the capacitor 110 to the op amp's inverting input terminal will be less than the voltage level $V_{ref}$ applied to the op amp non-inverting input terminal, and the op amp's output will be high. The subsequent upward transition of the clock signal φ1 will clock a high level into the flip-flop 118 and the flip-flop's state will remain high.

Conversely, if at this time the ramp signal $V_{ramp}$ is greater than the reference threshold $V_{thresh}$, then the voltage level applied by the capacitor 110 to the op amp's inverting input terminal will be greater than the voltage level $V_{ref}$ applied to the op amp' non-inverting input terminal, and the op amp's output will be low. The subsequent upward transition of the clock signal φ1 will clock a low level into the flip-flop 118 and the flip-flop will transition to a low state. This changes the control signals K and $\overline{K}$, which as discussed above inverts the polarity of the reference generator 64 and integrator amplifier 56.

Figure 6:
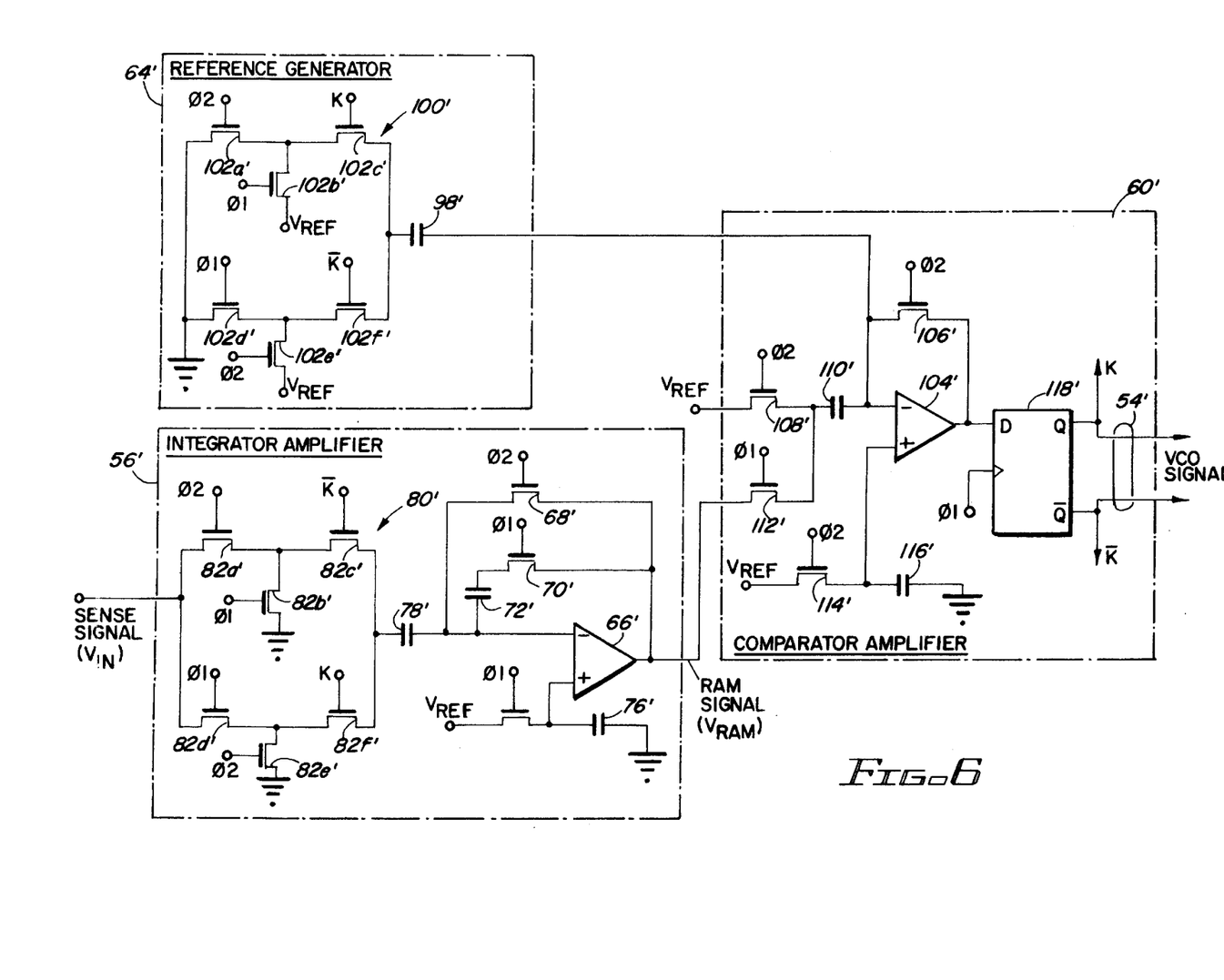
FIG. 6 is a schematic circuit diagram of a second embodiment of the VCO circuit of FIG. 2, this circuit like the circuit of FIG. 4 being implemented using switched-capacitor CMOS circuitry.

A schematic diagram of an alternative embodiment of the VCO circuit 50 is depicted in FIG. 6. This embodiment is implemented using CMOS circuitry and is similar to the embodiment depicted in FIG. 4 and described in detail above, except that it incorporates only two op amps, not three. This reduces the circuit's power consumption and reduces its generation of random noise. Individual electrical components in the FIG. 6 embodiment that correspond to components of the FIG. 4 embodiment are identified by the same reference numerals, except with an added prime mark.

Basically, the VCO circuit embodiment of FIG. 6 differs from the embodiment of FIG. 4 by substituting a simple passive capacitor divider circuit for the op amp 84 and related switching circuitry that comprise the reference generator 64 of FIG. 4. In particular, the signal output by the input circuit 100' of the reference generator 64' is coupled via the capacitor 98' directly to the inverting input terminal of the op amp 104' of the comparator amplifier 60'. Also coupled to this inverting input terminal is the voltage reference $V_{ref}$, via the FET 108' and capacitor 110'. This establishes a simple capacitor divider circuit. The reference threshold $V_{thresh}$ output on line 62' by the reference generator 64' thus corresponds to a predetermined fraction of the signal output by the input circuit 100', i.e., a predetermined fraction of $+V_{ref}$ or $-V_{ref}$. This fraction is determined by the ratio of the capacitances of the capacitors 110' and 98', i.e., $C_{110'}/(C_{98'}+C_{110'})$.

It will be appreciated that the VCO circuit embodiment of FIG. 6 is suitable for use only in circumstances where the reference threshold $V_{thresh}$ is desired to be less than the voltage reference $V_{ref}$. The use of this circuit topology enables power consumption to be reduced by about one third over that consumed by the circuit topology of FIG. 4.

It should be appreciated from the foregoing description that the present invention provides an improved apparatus and method for providing a measurement of the charge remaining in a battery used in an implantable device. The apparatus provides this measurement based not on the voltage level or impedance of the battery, but rather on a continuous measurement of the electrical current drawn from the battery, which is integrated over an integration time period. A precision current-sensing resistor provides a sense signal having a voltage that varies according to the magnitude of current being drawn, and this sense signal is integrated using a voltage-controlled oscillator circuit and counter, which is implemented using CMOS circuitry arranged in a switched-capacitor topology. This provides a digital measurement of depleted battery charge.

Although the invention has been described in detail with reference only to the presently preferred embodiment, those of ordinary skill in the art will appreciate that various modifications can be made without departing from the invention. Accordingly, the invention is defined only by the following claims.

What is claimed is:

1. A battery charge meter for use in monitoring the amount of charge delivered by a battery in an implantable device comprising:
   a sensor coupled to the battery, for providing a sense signal corresponding to the electrical current being drawn from the battery;
   a voltage-controlled oscillator circuit that generates a VCO signal having a frequency that corresponds to the sense signal; and
   a counter that counts the cycles of the VCO signal to produce a measurement of depleted battery charge.

2. The battery charge meter of claim 1, wherein the voltage-controlled oscillator circuit is configured using switched-capacitor CMOS circuitry.

3. The battery charge meter of claim 1, wherein the voltage-controlled oscillator circuit draws less than 100 nanoamperes of electrical current from the battery.

4. The battery charge meter of claim 1, wherein the sensor comprises a precision hybrid resistor.

5. The battery charge meter of claim 1, wherein each cycle of the VCO signal has a duration corresponding to a predetermined discrete quantity of charge depleted from the battery.

6. The battery charge meter of claim 1, wherein the voltage-controlled oscillator circuit includes:
   an integrator amplifier that integrates the sense signal to produce a ramp signal; and
   a comparator that compares the ramp signal with a prescribed threshold and reinitiates its integration of the sense signal each time the ramp signal reaches the threshold, wherein the comparator produces the VCO signal, and wherein the VCO signal changes its state each time the ramp signal reaches the threshold.

7. The battery charge meter of claim 1, further including a telemetry circuit for transmitting the measurement of depleted battery charge to a remote programmer device.

8. An implantable biomedical device, comprising:
   a biomedical circuit configured to monitor one or more parameters of a living body;
   a battery for supplying a time-varying electrical current to the biomedical circuit; and
   a battery charge delivery meter, including
   a sensor coupled to the battery, said sensor providing a sense signal corresponding to electrical current being drawn from the battery, and
   an integrator coupled to the sensor for integrating the sense signal to produce a measurement of the depleted battery charge over an integration time period.

9. The implantable biomedical device of claim 8, wherein the integrator is configured using switched-capacitor CMOS circuitry.

10. The implantable biomedical device of claim 8, wherein the integrator draws less than 100 nanoamperes of electrical current from the battery.

11. The implantable biomedical device of claim 8, wherein the sensor comprises a precision hybrid resistor.

12. The implantable biomedical device of claim 8, wherein the integrator includes:
   a voltage-controlled oscillator circuit that generates a VCO signal having a frequency that corresponds to the sense signal; and
   a counter that counts the cycles of the VCO signal, to produce the measurement of depleted battery charge.

13. The implantable biomedical device of claim 12, wherein each cycle of the VCO signal has a duration corresponding to a predetermined discrete quantity of charge depleted from the battery.

14. The implantable biomedical device of claim 12, wherein the voltage-controlled oscillator circuit includes:
   an integrator amplifier that integrates the sense signal to produce a ramp signal; and
   a comparator that compares the ramp signal with a prescribed threshold and reinitiates its integration of the sense signal each time the ramp signal reaches the threshold, wherein the comparator produces the VCO signal, and wherein the VCO signal changes its state each time the ramp signal reaches the threshold.

15. The implantable biomedical device of claim 8, further including a telemetry circuit for transmitting the measurement of depleted battery charge to a remote programmer device.

16. A battery charge delivery meter for a battery supplying an electrical current to a load circuit, comprising:

sensor means coupled to the battery, for providing a sense signal corresponding to the electrical current being drawn from the battery;

oscillator means for generating a sequence of signal pulses, wherein each signal pulse has a duration representing a predetermined discrete quantity of charge depleted from the battery; and     counter means for counting the signal pulses generated by the oscillator means, to produce the measurement of depleted battery charge.

17. The battery charge delivery meter of claim 16, wherein the oscillator means is configured using switched-capacitor CMOS circuitry.

18. A method for determining the charge in a battery that supplies a time-varying electrical current to a load circuit, comprising:

sensing the electrical current being drawn from the battery to provide a sense signal;

generating a sequence of signal pulses, wherein each signal pulse has a duration representing a predetermined discrete quantity of charge depleted from the battery; and     counting the signal pulses to produce a measurement of depleted battery charge.

\* \* \* \* \*